United States Patent [19]

Bonte et al.

[11] Patent Number: 5,470,579
[45] Date of Patent: Nov. 28, 1995

[54] XANTHINES, OPTIONALLY INCORPORATED IN LIPOSOMES, FOR PROMOTING SKIN OR HAIR PIGMENTATION

[75] Inventors: Frédéric Bonte, Courbevoie; Marc Dumas, Colombes; Alain Meybeck, Courbevoie; Christian Marechal, Paris, all of France

[73] Assignee: LVMH, Recherche, Colombes Cedex, France

[21] Appl. No.: 231,881

[22] Filed: Apr. 22, 1994

Related U.S. Application Data

[63] Continuation of Ser. No. 859,734, filed as PCT/FR90/00822, Nov. 16, 1990, abandoned.

[30] Foreign Application Priority Data

Nov. 28, 1989 [FR] France .................................. 89 15653

[51] Int. Cl.$^6$ ................... A61K 9/127; A61K 7/42
[52] U.S. Cl. .................... 424/450; 424/59; 424/70.1; 424/195.1; 424/401; 514/263; 514/264; 514/828; 514/944
[58] Field of Search .................. 424/59, 450, 195.1, 424/401, 70, 70.1; 514/263, 264, 828, 944

[56] References Cited

U.S. PATENT DOCUMENTS 5,165,935  11/1992  Andre et al. ........................ 424/450

FOREIGN PATENT DOCUMENTS 2609395  7/1988  France .

Primary Examiner—Jyothsna Venkat

[57] ABSTRACT

A method of treating skin or hair for promoting pigmentation wherein a xanthine component, in an amount effective to promote pigmentation, is incorporated in liposomes or hydrated lipidic lamellar phases.

43 Claims, No Drawings

XANTHINES, OPTIONALLY INCORPORATED IN LIPOSOMES, FOR PROMOTING SKIN OR HAIR PIGMENTATION

This application is a continuation of application No. 07/859,734, filed as PCT/FR90/00822, Nov. 16, 1990, now abandoned.

The present invention relates in general terms to the use of xanthines, optionally at least partially incorporated in hydrated lipidic lamellar phases or in liposomes, for the preparation of cosmetic or pharmaceutical compositions promoting skin or hair pigmentation.

The action of theophylline on melanocytes in culture has already been studied (Leising H. B. et al., Z. Naturforsch., 1977, 32C (7–8) 567–72). This study, limited to an in vitro experiment, revealed that the activity of theophylline in stimulating melanogenesis was sufficiently low to have dissuaded the commercial use of this compound in this application.

To obtain pigmenting compositions exhibiting a satisfactory activity, attempts were made to create synergistic effects by associating various substances. Thus Japanese patent application 62 045 527 describes compositions for preventing and treating gray hair which are based on cyclic AMP associated with various substances such as papaverine, theophylline or iso butylmethylxanthine.

Furthermore, the encapsulation of theophylline in liposomes has already been described. In particular, German patent application A-2 249 552 in the name of Inchema SA, also cited in Chemical Abstracts, volume 79, n°8, reference 45830t, describes the encapsulation of biologically active substances, especially theophylline, in liposomes. In this document, however, there is no mention at all of the activity of the substances in question on skin pigmentation.

It has now been discovered, totally unexpectedly, that certain xanthines or plant extracts in which they are present exhibit an advantageous activity on skin or hair pigmentation; it is this discovery which forms the basis of the present invention. It has also been discovered that this activity can be strongly potentiated by their incorporation in hydrated lipidic lamellar phases or in liposomes.

It has also been observed, unexpectedly, that the application of a composition containing one of these xanthines to the skin causes a greater thickening of the epidermis after exposure to solar radiation than in the absence of any application. This effect, added to that obtained independently on skin pigmentation, thus makes it possible to strengthen the skin's natural defenses against solar radiation.

Thus, according to a first feature, the present invention relates to the use of a xanthine of formula I below:

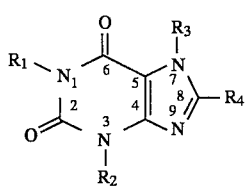

in which:

$R_1$ and $R_2$ are identical or different and are each a hydrogen atom, an alkyl radical with a linear, branched or cyclic chain, preferably having from 1 to 8 carbon atoms, an alkenyl radical with a linear or branched chain, preferably having from 2 to 5 carbon atoms, an alkynyl radical preferably having from 2 to 3 carbon atoms or an aralkyl radical preferably having from 7 to 12 carbon atoms, said alkyl, alkenyl and aralkyl radicals being unsubstituted or substituted by one or more halogen atoms or by one or more groups —$OR_5$, in which $R_5$ is a hydrogen atom or an alkyl radical having from 1 to 6 carbon atoms, preferably a methyl or ethyl radical;

$R_3$ is a hydrogen atom, an alkyl radical preferably having from 1 to 4 carbon atoms or a benzyl radical, said alkyl radical being unsubstituted or substituted by a heterocyclic radical such as the morpholine or radical, piperidin-1-yl or by one or more halogen atoms or hydroxyl groups; and $R_4$ is a hydrogen or halogen atom, an alkyl radical with a linear, branched or cyclic chain, preferably having from 1 to 6 carbon atoms, an aryl radical or a group

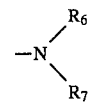

in which $R_6$ and $R_7$ independently are a hydrogen atom or an alkyl radical having from 1 to 6 carbon atoms, preferably a methyl or ethyl radical, or else they form together, with the nitrogen atom, a heterocycle, preferably a saturated monocyclic heterocycle, said alkyl or aryl radicals being unsubstituted or substituted by one or more halogen atoms or hydroxyl, methoxy, carbomethoxy or amino groups; or the use of a pharmaceutically or cosmetically acceptable salt of said xanthine, or that of a plant extract in which such a xanthine is present, for the preparation of a cosmetic or pharmaceutical composition, especially a dermatological composition, or in a method of promoting skin or hair pigmentation or for strengthening the skin's natural defenses against solar radiation.

According to one particular embodiment of the invention, the xanthine used or in a method of said preparation of a cosmetic or pharmaceutical composition, especially a dermatological composition, is a xanthine of formula I mentioned above in which: $R_1$ is a hydrogen atom or a methyl, ethyl, propyl, butyl, isobutyl, pentyl, isopentyl, 2-propenyl, 2-propynyl, benzyl, hydroxymethyl, 2-hydroxyethyl, 2-hydroxypropyl or 3-hydroxypropyl radical, $R_2$ is a hydrogen atom or a methyl, ethyl, propyl, iso propyl, butyl, isobutyl, isopropyl, prop-2-enyl, 2-methyl-2-propenyl, cyclohexyl, benzyl or 2,3-dibromopropyl radical, $R_3$ is a hydrogen atom or a methyl, chloromethyl, hydroxymethyl, 2-chloroethyl, morpholinomethyl or benzyl radical and $R_4$ is a hydrogen or bromine: atom or a methyl, ethyl, cyclopropyl, cyclopentyl, cyclohexyl, tert-butyl, 2-carbomethoxyethyl, hydroxymethyl, methoxymethyl, methylamino or piperidin-1-yl radical.

The following xanthines may be mentioned as examples of the xanthines of formula I mentioned above, used according to said particular embodiment:

xanthine,
1,8-dimethyl-3-isobutylxanthine,
7-benzyl-1,8-dimethyl-3-isobutylxanthine,
1-(2-hydroxyethyl)-3-isobutyl-8-methylxanthine,
1,8-dimethyl-3-(2-methyl-2-propenyl)xanthine,
3-(2,3-dibromopropyl)-1-ethyl-8-methylxanthine,
1,3-di(2-propenyl)-8-methylxanthine,
7-benzyl-8-bromo-3-isobutyl-1-methylxanthine,
8-ethyl-1-(2-hydroxyethyl)-3-isobutylxanthine,
8-hydroxymethyl-3-isobutyl-1-methylxanthine,
3-isobutyl-8-methoxymethyl-1-methylxanthine,
8-(2-carbomethoxyethyl)-3-isobutyl-1-methylxanthine,
3-isobutyl-1-methyl-8-tert-butylxanthine, 3-isobutyl-1-methyl-8-methylaminoxanthine,
1,3-dipropyl-8-(piperidin-1-yl)xanthine,
8-cyclopropyl-1,3-dipropylxanthine,
8-cyclopentyl-1,3-dipropylxanthine,
8-cyclohexyl-1,3-dipropylxanthine,
1,3-dimethyl-8-phenylxanthine,
1,3-dipropyl-8-phenylxanthine,
8-(2-amino-4-chlorophenyl)-1,3-dipropylxanthine,
1,3-diethyl-7-methylxanthine,
1,3-dipropyl-7-methylxanthine,
7-chloromethyl-1,3-dimethylxanthine,
1,3-dimethyl-7-hydroxymethylxanthine,
1,3-dimethyl-7-(morpholinomethyl)xanthine,
1,3,7-triethylxanthine,
3,7-diethyl-1-(prop-2-ynyl)xanthine and
7-(2-chloroethyl)-1,3-dimethylxanthine.

Of the xanthines in the above list, those which are preferred for carrying out the present invention are:
1,8-dimethyl-3-isobutylxanthine,
8-(2-carbomethoxyethyl)-3-isobutylxanithine and
3-isobutyl-1-methyl-8-tert-butylxanthine.

However, it has now been discovered, totally unexpectedly, that a xanthine of formula I mentioned above in which $R_3$ and $R_4$ are each a hydrogen atom gives the cosmetic or pharmaceutical composition, especially the dermatological composition, in which it is incorporated a greater activity on skin or hair pigmentation or on the strengthening of the skin's natural defenses against solar radiation.

Thus, according to one preferred embodiment of the invention, the xanthine used for the preparation of a cosmetic or pharmaceutical composition, especially a dermatological composition, is a xanthine of formula I mentioned above in which:

$R_1$ and $R_2$ are each independently of one another a hydrogen atom or a radical as defined above, and $R_3$ and $R_4$ are each a hydrogen atom.

The following xanthines may be mentioned as examples in the context of this preferred embodiment:
3-isobutyl-1-methylxanthine:
3-benzyl-1-methylxanthine,
3-isopentyl-1-methylxanthine,
1-methyl-3-(2-propenyl)xanthine,
1-methyl-3-(2-methyl-2-propenyl)xanthine,
3-butyl-1-methylxanthine,
1,3-diethylxanthine,
1-ethyl-3-propylxanthine,
3-butyl-1-ethylxanthine,
1-ethyl-3-(2-methylprop-2-enyl)xanthine,
3-cyclohexyl-1-ethylxanthine,
1-(2-hydroxyethyl)-3-isobutylxanthine,
1,3-dipropylxanthine,
1,3-di(2-propenyl)xanthine,
1,3-dibutylxanthine,
3-ethyl-1-pentylxanthine and
1-benzyl-3-isobutylxanthine.

Of the xanthines in the above list, those which are preferably used according to the present invention are:
3-isobutyl-1-methylxanthine,
3-benzyl-1-methylxanthine,
1,3-diethylxanthine,
1-ethyl-3-propylxanthine,
3-butyl-1-ethylxanthine,
1,3-dipropylxanthine and
1,3-dibutylxanthine.

According to one modified embodiment, the above-mentioned xanthine is selected from 1,3-dimethylxanthine and 3,7-dimethylxanthine.

According to another modified embodiment, the above-mentioned xanthine is 3-isobutyl-1-methylxanthine.

According to another embodiment, the xanthine used according to the present invention is a xanthine of formula I mentioned above in which:

$R_3$ and $R_4$ are each a hydrogen atom and $R_1$ and $R_2$ are a hydrogen atom or a radical as defined above, it being understood that at least $R_1$ or $R_2$ is a hydrogen atom. In particular, when $R_2$, $R_3$ and $R_4$ are each a hydrogen atom, $R_1$ is an alkyl radical preferably having from 1 to 4 carbon atoms, especially a methyl, ethyl, propyl or butyl radical and preferably a methyl radical.

Finally, according to a particularly preferred embodiment of the present invention, the xanthine used is a xanthine of formula I mentioned above in which:

$R_1$, $R_3$ and $R_4$ are each a hydrogen atom and $R_2$ is a radical as defined above, in particular an alkyl radical preferably having from 1 to 4 carbon atoms. In this case $R_2$ is preferably a methyl, propyl, butyl or isobutyl radical.

According to the present invention, the above-mentioned xanthines can be obtained by synthesis. Some of them are commercially available. Some of them are also present in plant extracts. As plants from which the xanthines can be obtained, there may be mentioned, in particular, cacao beans, tea leaves, maté(=Ilex paraguariensis) and cola beans, in particular Cola nitida and Cola verticillata. Methods of synthesizing xanthines are described in German patent 1 245 969; Ann. Chem., (1966), vol. 697, p. 142, to 158; Chem. Ber., (1953), vol. 86, p. 321–33; J. Chem. Soc., (1950), p. 1884–8; J. Org. Chem., (1980), p. 1711–13, vol. 45, n°9; British patent 982 079; East German patent 8 957; Soviet patent 115 947 (Chem. Abstr., vol. 53, 15 107-H); J. Gen. Chem. (USSR), (1946), vol. 16, p. 179–86 (Chem. Abstr., vol. 41, 96-d); J. Applied Chemistry, (1940), vol. 13, p. 1461–3; Chem. Ber., (1947), vol. 80, p. 401–5; international patent application WO-A2- 87/04435; Bull. Chem. Soc. Japan, (1973), vol. 46, n°2, p. 506–509; and J. Chem. Soc., (1962), p. 1866.

The pharmaceutically or cosmetically acceptable salts of the xanthines of formula I are salts which are non-toxic to man in the context of the uses according to the invention, such as, for example, alkali metal salts such as sodium or potassium salts, ammonium salts, salts of organic bases such as ethanolamine, diethanolamine, ethylenediamine, isopropylamine, triethanolamine, octadecylamine or choline, or a salt of an amino acid such as glycine or lysine. These salts are obtained by conventional methods well known to those skilled in the art, for example by reacting the xanthine with the base, generally in the presence of a solvent.

According to one particular embodiment of the present invention, at least one xanthine of formula I mentioned above, or one of its salts as defined above, is used in combination with at least one plant extract mentioned above.

According to one particular characteristic of the invention, the total concentration of compounds of formula I mentioned above, or their salts, or plant extracts in which they are present, is between 0.001% and 10% by weight, preferably between 0.01 and 1% by weight, relative to the total weight of the composition.

According to a second feature of the invention, the compound of formula I mentioned above, or one of its cosmetically or pharmaceutically acceptable salts, or the plant extract in which such a compound is present, or a combination of the above-mentioned compound and extract, is at least partially incorporated in hydrated lipidic lamellar phases or in liposomes.

According to a third feature;, the present invention further relates to a cosmetic or pharmaceutical composition, especially a dermatological composition, for promoting skin or hair pigmentation, said composition comprising at least one compound of formula I or one of its salts as defined above, or at least one plant extract containing a compound of formula I mentioned above, or a combination of the above-mentioned compound and extract, in a cosmetically or pharmaceutically acceptable excipient, vehicle or carrier.

According to a fourth feature, the present invention further relates to a cosmetic or pharmaceutical composition, especially a dermatological composition, for promoting skin or hair pigmentation, said composition comprising at least one compound of formula I or one of its salts as defined above, or at least one plant extract containing a compound of formula I mentioned above, or a combination of the above-mentioned compound and extract, at least partially incorporated in hydrated lipidic lamellar phases or in liposome-type vesicles, in a cosmetically or pharmaceutically acceptable excipient, vehicle or carrier.

According to a fifth feature, the present invention further relates to a cosmetic or pharmaceutical composition, especially a dermatological composition, particularly for strengthening the natural protection against the harmful effects of solar radiation or ultraviolet radiation, said composition comprising at least one compound of formula I or one of its salts as defined above, or at least one plant extract containing a compound of formula I mentioned above, or a combination of the above-mentioned compound and extract, in a cosmetically or pharmaceutically acceptable excipient, vehicle or carrier.

According to a sixth feature, the present invention further relates to a cosmetic or pharmaceutical composition, especially a dermatological composition, particularly for strengthening the natural protection against the harmful effects of solar radiation or ultraviolet radiation, said composition comprising at least one compound of formula I or one of its salts as defined above, or at least one plant extract containing a compound of formula I mentioned above, or a combination of the above-mentioned compound and extract, at least partially incorporated in hydrated lipidic lamellar phases or in liposome-type vesicles, in a cosmetically or pharmaceutically acceptable excipient, vehicle or carrier.

Also, according to a seventh feature, the present invention further relates to a pharmaceutical composition, especially a dermatological composition, particularly for treating skin or hair pigmentation disorders and more particularly for promoting the biosynthesis of melanin, said composition comprising at least one compound of formula I or one of its salts as defined above, or at least one plant extract containing a compound of formula I mentioned above, or a combination of the above-mentioned compound and extract, in a pharmaceutically acceptable excipient, vehicle or carrier.

According to an eighth feature, the present invention further relates to a pharmaceutical composition, especially a dermatological composition, for treating skin or hair pigmentation disorders and more particularly for promoting the biosynthesis of melanin, said composition comprising at least one compound of formula I or one of its salts as defined above, or at least one plant extract containing a compound of formula I mentioned-above, or a combination of the above-mentioned compound and extract, at least partially incorporated in hydrated lipidic lamellar phases or in liposomes, in a pharmaceutically acceptable excipient, vehicle or carrier.

In general the total concentration of the compounds, their salts or the extracts used according to the present invention, which are non-incorporated or at least partially incorporated in hydrated lipidic lamellar phases or in liposome-type vesicles, is between 0.001% and 10% by weight, preferably between 0.01% and 1% by weight, relative to the total weight of the final composition. The cosmetic or pharmaceutical compositions, especially the dermatological compositions, according to the invention can be applied topically for promoting skin and hair pigmentation or for strengthening the skin's natural defenses, in particular as compositions in the form of a cream, gel or lotion for topical application to the skin or hair.

Thus the cosmetic or pharmaceutical compositions, especially the dermatological compositions, according to the invention find various applications in cosmetology or dermatology since it is desirable to increase the pigmentation or strengthen the natural defenses of the skin or hair. For example, these compositions can be used as sun products for accelerating or intensifying tanning, which, in addition to the often desirable esthetic advantage, makes it possible to strengthen the natural defenses against ultraviolet radiation by increasing the amount of melanin in the epidermis and thickening the epidermis. These compositions can also be used for example in the form of a cream to give the skin a more sunburnt appearance, or else in the form of a lotion for preventing and treating gray hair. Furthermore, in dermatology, the compositions according to the present invention can be used as therapeutic agents, by themselves or in association with other drugs, in particular by topical application in the treatment of melanogenesis dysfunctions, for example for treating vitiligo.

Also, according to a ninth feature, the present invention further relates to a process for the manufacture of a cosmetic or pharmaceutical composition, especially a dermatological composition, for promoting skin or hair pigmentation, said process comprising initially the at least partial incorporation of at least one compound of formula I or one of its salts as defined above, or at least one plant extract in which it is present, or a combination of the above-mentioned compound and extract, which is then mixed with a cosmetically or pharmaceutically acceptable excipient, vehicle or carrier.

According to a tenth feature, the present invention further covers a process for the manufacture of a cosmetic or pharmaceutical composition, especially a dermatological composition, for promoting skin or hair pigmentation, said process comprising initially the at least partial incorporation of at least one compound of formula I or one of its salts as defined above, or at least one plant extract in which it is present, or a combination of the above-mentioned compound and extract, into hydrated lipidic lamellar phrases or into liposome-type vesicles, which are then mixed with a cosmetically or pharmaceutically acceptable excipient, vehicle or carrier.

According to an eleventh feature, the present invention aims to cover a method of treating the skin or hair for promoting pigmentation, said method comprising the application, in an mount effective for producing pigmentation, of at least one compound of formula I or one of its salts as defined above, or at least one plant extract in which it is present, or a combination of the above-mentioned compound and extract, the whole being introduced into a cosmetically or pharmaceutically acceptable excipient, vehicle or carrier.

According to a twelfth feature, the present invention further aims to cover a method of treating the skin or hair for promoting pigmentation, said method comprising the application, in an amount effective for producing pigmentation, of at least one compound of formula I or one of its salts as defined above, or at least one plant extract in which it is present, or a combination of the above-mentioned compound and extract, at least partially incorporated in hydrated lipidic lamellar phases or in liposome-type vesicles, the whole being optionally incorporated into a cosmetically or pharmaceutically acceptable excipient, vehicle or carrier.

According to a thirteenth feature, the present invention further covers a method of treating the skin for strengthening the natural protection against the harmful effects of solar radiation or ultraviolet radiation, said method comprising the application to the skin, in an amount effective for producing natural protection against the harmful effects of solar radiation or ultraviolet radiation, of at least one compound of formula I or one of its salts as defined above, and at least one plant extract in which it is present, or a combination of the above-mentioned compound and extract, optionally incorporated into a cosmetically or pharmaceutically acceptable excipient, vehicle or carder.

Finally, according to a fourteenth feature, the present invention further aims to cover a method of treating the skin for strengthening the natural protection against the harmful effects of solar radiation or ultraviolet radiation, said method comprising the application to the skin, in an amount effective for strengthening the natural protection against the harmful effects of solar radiation or ultraviolet radiation, of at least one compound of formula I or one of its salts as defined above, or at least one plant extract in which it is present, or a combination of the above-mentioned compound and extract, at least partially incorporated in hydrated lipidic lamellar phases or in liposome-type vesicles, the whole being optionally incorporated into a cosmetically or pharmaceutically acceptable excipient, vehicle or carrier.

In the present description and the claims, the expression "at least partially incorporated in hydrated lipidic lamellar phases or in liposome-type vesicles" is understood as meaning that the compound of formula I (or the plant extract in which it is present) is combined with hydrated lipidic lamellar phases or with liposomes, irrespective of the form of this combination. However, a preferred combination consists in the incorporation or encapsulation of the compound of formula I (or the plant extract in which it is present) in hydrated lipidic lamellar phases or in liposome-type vesicles, although it is not necessary for the total amount to be incorporated or encapsulated in order to achieve the desired pigmentation effect according to the invention.

The term "lipidic" in the expression "lipidic lamellar phase" covers all substances comprising a so-called fatty hydrocarbon chain generally containing more than 5 carbon atoms, this substance usually being referred to as a "lipid".

According to the invention the lipids used to form either the lipidic lamellar phases or the liposome-type vesicles are amphiphilic lipids, i.e. lipids consisting of molecules possessing a hydrophilic group, which can equally well be ionic or non-ionic, and a lipophilic group, these amphiphilic lipids being capable of forming lipidic lamellar phases or liposome-type vesicles in the presence of an aqueous phase.

The following may be mentioned in particular among these lipids: phospholipids, phosphoaminolipids, glycolipids, polyethoxylated fatty alcohols and polyethoxylated or non-polyethoxylated polyol esters. Such substances consist for example of a hydrogenated or non-hydrogenated egg or soya lecithin, a phosphatidylcholine, a phosphatidylserine, a sphingomyelin, a cerebroside or an ethoxylated polyglycerol stearate.

The compounds used according to the present invention can be incorporated into hydrated lipidic lamellar phases or into liposomes by known preparative techniques described for example in French patent application A- 2521 565, if appropriate in combination with French patent application A- 2 534 487.

According to the present invention, it has been found, totally unexpectedly, that not all the xanthines of formula I mentioned above possess equivalent activities, in particular on skin or hair pigmentation.

Such xanthines substituted in the 1-position and/or 3-position are much more active than the others, in particular than some of them which are also substituted in the 7-position, such as caffeine (1,3,7-trimethylxanthine).

Moreover, encapsulation in hydrated lipidic lamellar phases or in liposomes radically potentiates the activity of these xanthines substituted in the 1-position and/or 3-position, whereas the activity of the xanthines substituted in the 7-position remains very substantially lower. This potentiation was observed by means of tests performed in vivo.

Thus the discovery of the strong pigmenting activity of the xanthines substituted in the 1-position and/or 3-position is a complete surprise to those skilled in the art.

Further objects, characteristics and advantages of the invention will become clearly apparent from the following explanatory description referring to several Examples, which are given simply by way of illustration and cannot therefore in any way limit the scope of the invention.

In the Examples the percentages are given by weight, unless indicated otherwise.

EXAMPLE 1

Preparation of liposomes containing a xanthine according to the invention

Being of hydrophobic character, the xanthines are preferably incorporated in the lipidic phase.

This is done for example by the following procedure:

0.2 g of 3-isobutyl-1-methylxanthine (IBMX), 3.6 g of soya lecithin and 0.4 g of β-sitosterol are dissolved in 25 ml of methylene chloride. This organic solution is evaporated in a rotating round-bottomed flask at 45° C. under reduced pressure to give a lipidic film deposited on the inner wall of the flask.

The film obtained is taken up in 95.8 g of distilled water or buffer solution to give a suspension of lipidic vesicles. Sonication is carried out at 100 W for 10 min at 4° C. to give liposomes having a mean vesicle size of 142 nm, which at least partially encapsulate the IBMX.

The same procedure can be followed with other xanthines according to the present invention, as defined above.

The stimulation of melanogenesis in animals in vivo is demonstrated in Example 2 below.

EXAMPLE 2

Demonstration of the increase in melanogenesis in animals with IBMX

Adult tricolored guinea-pigs are used which are divided into 4 groups of 3 or 4 guinea-pigs. The following procedure is adopted:

Before and during the experiment, the right and left sides of the guinea-pigs are carefully shaved every day for the first 5 days (period of exposure to UV) and then every 2 days until the end of the study.

For each animal comparably pigmented patches, most frequently of light brown appearance, are determined on each side. 10 min before each exposure to ultraviolet rays, about 0.05 g of test product or control product, depending on the group, is applied to one of the two sides, selected at random at the start of the experiment, the other side being exposed "bare" by way of control.

The applications are continued under the same conditions over the 12 days following the fifth exposure to UV.

The exposure to ultraviolet radiation is effected by means of a solar simulator delivering 86% of UVA and 14% of UVB, for 5 min on the first day, 10 min on the second day, 15 min on the third day and 20 min on the fourth and fifth days.

12 days after the last exposure a fragment of skin is taken from the untreated but exposed side and from the other, treated and exposed side.

The skin fragments are then subjected to a histological examination.

This examination comprises on the one hand a study of the melanogenesis by Fontana's argentaffin method on 4 μm sections (Techniques d'histologie (Techniques in histology), Professor Chevreau, published by Maloine, 1977, page 157), and on the other hand an assessment of the thickness of the epidermis on 4 μm sections stained by Massoffs trichrome method (hematoxylin, acid fuchsin, Ponceau de xylidine, aniline blue).

To study the melanogenesis, two randomly selected zones of a pigmented patch, in which 25 malpighian cells are identified, are examined and the "activated" melanocytes among them, i.e. those containing an accumulation of melanin, are counted. The activation of the melanogenesis process is then expressed as the percentage of activated cells from the mean of these two values. The rhizomic forms of the melanocytes are also identified.

On these same zones, the amount of melanin in the other layers of the epidermis is examined and this amount is globally assessed on a 5-point scale from 0 to 4 according to whether the amount of melanin formed is zero, small, moderate, large or very large, respectively.

Finally, the thickness of the epidermis is measured on these zones by means of a micrometer on a binocular microscope.

The results of the histological study have been collated in Table I, which shows the percentage activation and makes it possible to assess the variations in the amount of melanin formed (mean values according to the scale defined above) and in the thickness of the epidermis (expressed in μm).

The test products are as follows:

| product "$I_1$": | gelled suspension of liposomes |
|---|---|
| | containing 0.1% of IBMX, prepared according to Example 9 |
| product "$I_2$": | gelled solution of IBMX |
| | IBMX 0.1 g |
| | ethanol 30.0 g |
| | double-distilled water 19.9 g |
| | Carbopol 940 ® gel, 1% 50.0 g |
| product "$A_1$": | gelled suspension of control liposomes ("empty" liposomes) |
| | Composition per 100 g: |
| | soya lecithin 1.8 g |
| | β-sitosterol 0.2 g |
| | distilled water 48.0 g |
| | Carbopol 940 ® gel, 1% 50.0 g |
| product "$A_2$": | ethanolic Carbopol ® gel |
| | ethanol 30.0 g |
| | distilled water 20.0 g |
| | Carbopol 940 ® gel, 1% 50.0 g |

The results indicated in Table I confirm the pronounced activity of IBMX, and more particularly that of IBMX encapsulated in liposomes according to the invention, on melanogenesis in animals.

TABLE I

| | Activated melanocytes % | | Amount of malanin formed | | Thickness of the epidermis (μm) | | Melanocytes of rhizomic appearance % | |
|---|---|---|---|---|---|---|---|---|
| | CS | TS | CS | TS | CS | TS | CS | TS |
| $I_1$ (0.1% of IBMX encapsulated in liposomes, in gel) | 55.71 | 90.00 | 1.50 | 3.50 | 9.92 | 13.29 | 0 | 100 |
| $I_2$ (0.1% of IBMX in gel) | 35.14 | 77.71 | 0.64 | 2.21 | 8.43 | 9.50 | 0 | 10 |
| $A_2$ ("empty" liposomes in gel) | 36.67 | 87.00 | 0.91 | 2.50 | 7.75 | 8.50 | 0 | 0 |
| $A_2$ (gel) | 32.86 | 78.86 | 0.43 | 2.14 | 9.36 | 8.43 | 0 | 0 |

CS: control side, untreated
TS: treated side

It is seen from Table I that all the results obtained with IBMX encapsulated in liposomes ($I_1$) are superior to those obtained with the other products tested. This is particularly striking as regards the amount of melanin formed and even more so as regards the rhizomic appearance of the melanocytes. It is emphasized that when the melanocyte is activated and when it produces melanin in the form of melanosomes, the shape of the melanocyte changes so as to form kinds of "tentacles", generally referred to as "dendrites"; the appearance of the melanocyte is said to be "rhizomic". The melanic pigments are then led by the dendrites towards the upper layers of the epidermis. The "rhizomic" appearance is therefore an excellent criterion for demonstrating the activity of the melanogenesis. When at rest, on the other hand, the melanocytes lose this appearance and resume a more regular shape. Therefore Table I further shows that IBMX in the free form in an ethanolic gel ($I_2$) is also more active than the two control products ($A_1$) and ($A_2$).

The thickness of the epidermis, which is to be correlated with the organism's defense against ultraviolet radiation, is also greater in the animals treated with IBMX encapsulated in liposomes according to the invention (I).

EXAMPLE 3

Demonstration of the increase in melanogenesis in animals with different xanthines The protocol described in Example 2 is followed with the products below:

product "$I_3$": 0.05% gelled solution of 3-methylxanthine prepared like product $I_2$ of Example 2 product "$I_4$": 0.05% gelled solution of 1-methylxanthine prepared like product $I_2$ of Example 2 product "$I_5$": 0.05% gelled solution of 3,7-dimethylxanthine prepared like product $I_2$ of Example 2 product "$I_6$": gelled suspension of liposomes containing 0.1% of 1,3-dimethylxanthine prepared according to Example 9

The results are shown in Table I

TABLE II

|  | Activated melanocytes % | | Amount of melanin formed | | Thickness of the epidermis (μm) | | Melanocytes of rhizomic appearance % | |
|---|---|---|---|---|---|---|---|---|
|  | CS | TS | CS | TS | CS | TS | CS | TS |
| $I_3$ | 26.63 | 85.91 | 0.16 | 2.22 | 7.21 | 10.07 | 0 | 80 |
| $I_4$ | 27.70 | 82.10 | 0.06 | 1.87 | 8.24 | 11.19 | 0 | 60 |
| $I_5$ | 32.14 | 86.50 | 0.20 | 1.95 | 8.80 | 10.32 | 0 | 30 |
| $I_6$ | 35.60 | 73.70 | 0.69 | 2.09 | 9.73 | 11.23 | 0 | 30 |

CS: control side, untreated
TS: treated side

The experimental results obtained in vivo for products $I_1$ to $I_6$ clearly show a very significant activity on the stimulation of skin pigmentation via an action on the melanocytes. It will be observed that products $I_3$ and $I_4$ produce the best results. Here again a thickening of the epidermis with the products of the invention will be noted, tending to promote the natural defenses against solar radiation.

Various Examples of the formulation of cosmetic or pharmaceutical compositions, especially dermatological compositions, active in the treatment of skin pigmentation disorders, will be given below.

EXAMPLE 4

| Aqueous gel for tanning the face | |
|---|---|
| IBMX | 0.1 g |
| Ethanol | 30.0 g |
| Distilled water | 19.9 g |
| Carbopol ® 940 gel, 1% | qsp 100 g |

EXAMPLE 5

| Tanning sun cream | |
|---|---|
| 3-Methylxanthine | 0.05 g |
| Isocetyl stearate | 8.0 g |
| Hydrogenated groundnut oil | 10.0 g |
| Lanolin oil | 3.5 g |
| Cetyl alcohol | 5.0 g |
| Stearyl alcohol | 2.5 g |
| Light liquid petrolatum | 10.0 g |
| Neutralized phosphoric acid monoester of cetyl alcohol EO | 3.0 g |

This phase is emulsified with an aqueous phase, qsp 100 g, containing:

| | |
|---|---|
| Pantothenol | 0.1 g |
| Preservatives | 0.2 g |
| Water-soluble sun filter | 5.0 g |

EXAMPLE 6

| Lotion for strengthening the natural solar protection | |
|---|---|
| Alcohol | 42.5 g |
| Propylene glycol | 3.0 g |
| Menthol | 0.05 g |
| Hydroxypropyl methyl cellulose | 1.5 g |
| 1-Methylxanthine (dry weight) | 0.2 g |
| Fragranced aqueous excipients | qsp 100 g |

This lotion is applied locally, preferably twice a day, every day for 3 to 8 days, preceding prolonged exposure to the sun.

EXAMPLE 7

| Hair tonic lotion for treating gray hair | |
|---|---|
| IBMX | 0.2 g |
| Alcohol | 60.0 g |
| Water | 37.0 g |
| Fragranced excipients | qsp 100 g |

This lotion can be applied to the hair and scalp twice a day for two-month treatments.

EXAMPLE 8

| Dermatological cream for treating vitiligo | |
|---|---|
| IBMX | 0.5 g |
| Soya lecithin | 1.5 g |
| Perhydrosqualene | 83.0 g |

These constituents are heated in a water bath at 70° C. for 15 min. 50 g of the resulting oily phase are taken up in 225 ml of double-distilled water. The mixture is stirred by means of a Raynefie stirrer and then gelled with 125 g of a Carbopol® 940 gel having the composition shown in Example 9 below. This gives a cream, which is used once to twice a day by local application to depigmented zones.

EXAMPLE 9

Preparation of a gel from a liposomal suspension of BMX 50 g of the Carbopot® 940 gel having the following composition are mixed with 50 g of the homogenized suspension obtained in Example 1:

| | |
|---|---|
| Carbopol 940 ® | 2.0 g |
| Nipagin M ® | 0.35 g |
| Nipasol ® | 0.02 g |
| Dissolvine ® | 0.005 g |
| Triethanolarmine | 2.50 g |
| Glycerol | 3.0 g |
| Distilled water | qsf 100 g |

This gel can be used by local application, for example to strengthen the natural solar protection.,

EXAMPLE 10

Preparation of a cosmetic pigmenting composition based on a natural extract containing theobromine
Preparation of the cacao extract The cacao extract is obtained from cacao beans by a method of extraction based on that described in U.S. Pat. No. 2,275,835, and in particular on that of the Examples. This extract contains a mixture of theobromine and caffeine.

| Cosmetic composition: | |
|---|---|
| cacao extract | 1.0 g |
| ethanol | 29.0 g |
| distilled water | 20.0 g |
| Carbopol 940 ® gel, 1% | 50.0 g |
| | 100.0 g |

This composition can be used as described in Example 9.

Of course, the invention includes all the means constituting technical equivalents to the means described, as well as the various combinations thereof.

What is claimed is:

1. A method of treating the skin or hair for promoting pigmentation, said method comprising applying to said skin or hair to be pigmented, in an amount effective to producing pigmentation, at least one xanthine component incorporated in liposomes or in hydrated lipidic lamellar phases, (a) where in the xanthine has the formula (I) below:

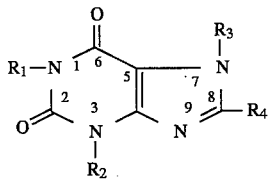

in which:

$R_1$ and $R_2$ are identical or different and are each a hydrogen atom, a linear or branched alkyl radical having from 1 to 8 carbon atoms or a cyclo alkyl radical having from 3 to 8 carbons atoms, an alkenyl radical with a linear or branched chain having from 2 to 5 carbon atoms, an alkynyl radical having from 2 to 3 carbon atoms or an aralkyl radical having from 7 to 12 carbon atoms, said alkyl, alkenyl and aralkyl radicals being unsubstituted or substituted by one or more halogen atoms or by one or more groups—$OR_5$ in which $R_5$ is a hydrogen atom or an alkyl radical having from 1 to 6 carbon atoms, $R_3$ is a hydrogen atom, an alkyl radical having from 1 to 4 carbon atoms or a benzyl radical, said alkyl radical being unsubstituted or substituted by heterocyclic radical morpholin-4-yl piperidin-1-yl radical or by one or more halogen atoms or hydroxyl groups, and $R_4$ is a hydrogen or halogen atom, a linear or branched alkyl radical having 1 to 6 carbon atoms a cycloalkyl radical having 3–6 carbon atoms, radical being unsubstituted or substituted by one or more halogen atoms hydroxyl, methoxy, carbomethoxy or amino groups, or, $R_4$ is the group:

in which $R_6$ and $R_7$ independently are a hydrogen atom or an alkyl radical having from 1 to 6 carbon atoms, or, $R_6$ and $R_7$ form together with said nitrogen atom, a piperidin-1-yl, said alkyl radicals being unsubstituted or substituted by one or more halogen atoms or hydroxyl, methoxy., carbomethoxy or amino groups, or (b) a pharmaceutically or cosmetically acceptable salt of said xanthine of formula (I).

2. The method of claim 1 wherein, in formula (I):

$R_1$ is a hydrogen atom, a methyl, ethyl, propyl, butyl, isobutyl, pentyl, isopentyl, 2-propenyl, 2-propynyl, benzyl, hydroxymethyl, 2-hydroxyethyl, 2-hydroxypropyl or 3-hydroxypropyl radical, $R_2$ is a hydrogen atom, a methyl, ethyl, propyl, isopropyl, butyl, isobutyl, isopropyl, 2-propenyl, 2-methyl-2-propenyl, cyclohexyl, benzyl or 2,3-dibromopropyl radical, $R_3$ is a hydrogen atom, a methyl, chloromethyl, hydroxymethyl, 2-chloroethyl, morpholinomethyl or benzyl radical and $R_4$ is a hydrogen, bromine atom or a methyl, ethyl, cyclopropyl, cyclopentyl, cyclohexyl, tert-butyl, 2-carbomethoxyethyl, hydroxymethyl, methoxymethyl, methylamino or piperidin-2-yl.

3. The method of claim 1 wherein the xanthine of formula (I) is selected from the group consisting of:
xanthine,
1,8-dimethyl-3-isobutylxanthine,
7-benzyl- 1,8-dimethyl-3-isobutylxanthine,
1-(2-hydroxyethyl)-3-isobutyl-8-methylxanthine,
1,8-dimethyl-3-(2-methyl-2-propenyl)xanthine,
3-(2,3-dibromopropyl)-1-ethyl-8-methylxanthine,
1,3-di(2-propenyl)-8-methylxanthine,
7-benzyl-8-bromo-3-isobutyl-1-methylxanthine,
8-ethyl-1-(2-hydroxyethyl)-3-isobutylxanthine,
8-hydroxymethyl-3-isobutyl-1-methylxanthine,
3-isobutyl-8-methoxymethyl-1-methylxanthine,
8-(2-carbomethoxyethyl)-3-isobutyl-1-methylxanthine,
3-isobutyl-1-methyl-8-tert-butylxanthine,
3-isobutyl-1-methyl-8-methylaminoxanthine,
1,3-dipropyl-8-piperidioxanthine,
8-cyclopropyl-1,3-dipropylxanthine,
8-cyclopentyl-1,3-dipropylxanthine,
8-cyclohexyl-1,3-dipropylxanthine, 1,3-dimethyl-8-phenylxanthine,
1,3-dipropyl-8-phenylxanthine,
8-(2-amino-4-chlorophenyl)-1,3-dipropylxanthine,
1,3-diethyl-7-methylxanthine,
1,3-dipropyl-7-methylxanthine,
7-chloromethyl-1,3-dimethylxanthine,
1,3-dimethyl-7-hydroxymethylxanthine,
1,3-dimethyl-7-(morpholinomethyl)xanthine,
1,3,7-triethylxanthine,
3,7-diethyl-1-(2-propynyl)xanthine and
7-(2-chloroethyl)-1,3-dimethylxanthine.

4. Method according to claim 3 wherein the xanthine is selected from the group consisting of:
1,8-dimethyl-3-isobutylxanthine,
8-(2-carbomethoxyethyl)-3-isobutylxanthine and
3-isobutyl-1-methyl-8-tert-butylxanthine.

5. The method of claim 1 wherein, in formula (I), $R_3$ and $R_4$ are each a hydrogen atom.

6. The method of claim 5 wherein the xanthine is selected from the group consisting of:
3-isobutyl-1-methylxanthine,
3-benzyl-1-methylxanthine,
3-isopentyl-1-methylxanthine,
1-methyl-3-(2-propenyl)xanthine,
1-methyl-3-(2-methyl-2-propenyl)xanthine,
3-butyl-1-methylxanthine,
1,3-diethylxanthine,
1-ethyl-3-propylxanthine,
3-butyl-1-ethylxanthine,
1-ethyl-3-(2-methyl-2-propenyl)xanthine,
3-cyclohexyl-1-ethylxanthine,
1-(2-hydroxyethyl)-3-isobutylxanthine,
1,3-dipropylxanthine,
1,3-di(2-propenyl)xanthine,
1,3-dibutylxanthine,
3-ethyl-1-pentylxanthine and
1-benzyl-3-isobutylxanthine.

7. The method of claim 6 wherein the xanthine is selected from the group consisting of:
3-isobutyl-1-methylxanthine,
3-benzyl-1-methylxanthine,
1,3-diethylxanthine,
1-ethyl-3-propylxanthine,
3-butyl-1-ethylxanthine,
1,3-dipropylxanthine and
1,3-dibutylxanthine.

8. The method of claim 1, wherein said xanthine component is selected from the group consisting of 1,3-dimethylxanthine and 3,7-dimethylxanthine.

9. The method of claim 1 wherein the xanthine is 3-isobutyl-1-methylxanthine.

10. The method of claim 1, wherein, in formula (I), $R_3$ and $R_4$ are each a hydrogen atom and $R_1$ and $R_2$ are each a hydrogen atom, a linear or branched alkyl radical having from 1 to 8 carbon atoms, cyclo-alkyl radical having from 3 to 8 carbon atoms, an alkenyl radical with a linear or branched chain having from 2 to 5 carbon atoms; an alkynyl radical having from 2 to 3 carbon atoms and an aralkyl radical having from 7 to 12 carbon atoms, said alkyl, alkenyl and aralkyl radicals being unsubstituted or substituted by one or more halogen atoms or by one or more groups —$OR_5$ in which $R_5$ is selected from the group consisting of a hydrogen atom and an alkyl radical having from 1 to 6 carbon atoms, at least one of $R_1$ and $R_2$ being a hydrogen atom.

11. The method of claim 10 wherein $R_2$, $R_3$ and $R_4$ are each a hydrogen atom and $R_1$ is an alkyl radical having from 1 to 4 carbon atoms.

12. The method of claim 1, wherein, in formula (I), $R_1$, $R_3$ and $R_4$ are each a hydrogen atom and $R_2$ is an alkyl radical having from 1 to 4 carbon atoms.

13. The method of claim 12, wherein $R_2$ is selected from the group consisting of a methyl, propyl, butyl and isobutyl radical.

14. The method of claim 1, wherein the pharmaceutically or cosmetically acceptable salt is selected from the group consisting of an alkali metal salt, a salt of an organic base, a choline salt, and a salt of an amino acid.

15. The method of claim 1 wherein the total concentration of the xanthine component ranges between 0.001% and 10% by weight, relative to the total weight of the composition.

16. The method of claim 1, wherein the total concentration of the xanthine component ranges between 0.01 an 1% by weight, relative to the total weight of the composition.

17. The method of claim 1, wherein said method causes thickening of the epidermis, thereby strengthening natural protection against the harmful effects of solar radiation or ultraviolet radiation.

18. The method of claim 1, which is a method for treating skin or hair pigmentation disorders and which is promoting the biosynthesis of melanine.

19. The method of claim 1, wherein said method comprises applying a plant extract containing at least one said xanthine component incorporated in liposomes or in hydrated lipidic lamellar phases where in said plant extract is selected from the group, consisting of cacao beans, tea leaves, Ilex paraguariensis, cola bean nitida and cola verticillata.

20. The method of claim 1, wherein $R_2$, $R_3$ and $R_4$ are each an hydrogen atom and $R_1$ is selected from the group consisting of a methyl, ethyl, propyl and butyl radical.

21. The method claim 1, wherein $R_1$, $R_3$ and $R_4$ are each a hydrogen atom and $R_2$ is selected from the group consisting of a methyl, propyl, butyl and isobutyl radical.

22. A method of treating the skin or hair for promoting pigmentation, said method comprising applying to said skin or hair to be pigmented, in an amount effective for producing pigmentation, at least one xanthine component incorporated in liposomes or in hydrated lipidic lamellar phases, wherein:

(a) a xanthine of the formula (I) below:

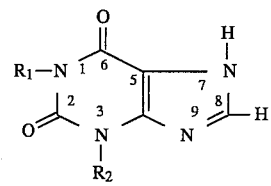

in which:
$R_1$ and $R_2$ are identical or different and are each a hydrogen atom, a linear or branched alkyl radical having from 1 to 8 carbon atoms a cyclo alkyl radical having 3–8 carbon atoms, at least one $R_1$ and $R_2$ being a hydrogen atom, or (b) a pharmaceutically or cosmetically acceptable salt of said xanthine of formula (I).

23. The method of claim 22, wherein said method causes thickening of epidermis, thereby strengthening natural protection against the harmful effects of solar radiation or ultraviolet radiation.

24. The method of claim 23, is a method for treating skin or hair pigmentation disorders which is promoting the biosynthesis of melanine.

25. The method of claim 22, wherein said method comprises applying a plant extract containing at least one said xanthine component incorporated in liposomes or in hydrated lipidic lamellar phases where in said plant extract is selected from the group consisting of cacao beans, tea leaves, Ilex paraguariensis, cola bean nitida and cola verticillata.

26. The method of claim 22, wherein $R_2$ is a hydrogen atom and $R_1$ is linear or branched alkyl radical having from 1 to 4 carbon atoms or a cyclo alkyl radical having 3 to 4 carbon atoms.

27. The method of claim 26, wherein $R_1$ is selected from the group consisting of a methyl, ethyl, propyl and butyl radical.

28. The method of claim 22, wherein $R_1$ is a hydrogen atom and $R_2$ is linear or branched alkyl radical having from 1 to 4 carbon atoms or a cyclo alkyl radical having 3 to 4 carbon atoms.

29. The method of claim 28, wherein $R_2$ is selected from the group consisting of a methyl, propyl, butyl and isobutyl radical.

30. The method of claim 22, wherein the total concentration of the xanthine component ranges between 0.001% and 10% by weight, relative to the total weight of the composition.

31. The method of claim 22, wherein the total concentration of the xanthine component ranges between 0.01 and 1% by weight, relative to the total weight of the composition.

32. A method of treating the skin or hair for promoting pigmentation, said method comprising applying to said skin or hair to be pigmented, in an amount effective for producing pigmentation, at least one xanthine component (a) wherein the xanthine is selected from the group consisting of:
1,8-dimethyl-3-isobutylxanthine,
7-benzyl-1,8-dimethyl-3-isobutylxanthine,
1-(2-hydroxyethyl)-3-isobutyl-8-methylxanthine,
1,8-dimethyl-3-(2- methyl-2-propenyl)xanthine,
3-(2,3-dibromopropyl)-1-ethyl-8-methylxanthine,
1,3-di(2-propenyl)-8-methylxanthine,
7-benzyl-8-bromo-3-isobutyl-1-methylxanthine,
8-ethyl-1-(2-hydroxyethyl)-3-isobutylxanthine,
8-hydroxymethyl-3-isobutyl-1-methylxanthine,
3-isobutyl-8-methoxymethyl-1-methylxanthine,
8-(2-carbomethoxyethyl)-3-isobutyl-1-methylxanthine,
3-isobutyl-1-methyl-8-tert-butylxanthine,
3-isobutyl-1-methyl-8-methylaminoxanthine,
1,3-dipropyl-8(piperidin-1-yl(xanthine)
8-cyclopropyl-1,3-dipropylxanthine,
8-cyclopentyl-1,3-dipropylxanthine,
8-cyclohexyl-1,3-dipropylxanthine,
1,3-dimethyl-8-phenylxanthine,
1,3-dipropyl-8-phenylxanthine,
8-(2-amino-4-chlorophenyl)-1,3-dipropylxanthine,
1,3-diethyl-7-methylxanthine,
1,3-dipropyl-7-methylxanthine,
7-chloromethyl-1,3-dimethylxanthine,
1,3-dimethyl-7-hydroxymethylxanthine,
1,3-dimethyl-7-(morpholin-4-yl-methyl)xanthine,
1,3,7-triethylxanthine,
3,7-diethyl-1-(2-propynyl)xanthine
7-(2-chloroethyl-1,3-dimethylxanthine
3-benzyl-1-methylxanthine,
3-isopentyl-1-methylxanthine,
1-methyl-3-(2-propenyl)xanthine,
1-methyl-3-(2-methyl-2-propenyl)xanthine,
3-butyl-1-methylxanthine,
1,3-diethylxanthine,
1-ethyl-3-propylxanthine,
3-butyl-1-ethylxanthine,
1-ethyl-3-(2-methyl-2-propenyl)xanthine,
3-cyclohexyl-1-ethylxanthine,
1-(2-hydroxyethyl)-3-isobutylxanthine,
1,3-dipropylxanthine,
1,3-di-(2-propenyl)xanthine,
1,3-dibutylxanthine,
3-ethyl-1-pentylxanthine,
1-benzyl-3-isobutylxanthine,
1-methylxanthine,
1-ethylxanthine,
1-propylxanthine,
1-butylxanthine,
3-methylxanthine,
3-propylxanthine,
3-butylxanthine, and
3-isobutylxanthine; or (b) a pharmaceutically or cosmetically acceptable salt of said xanthine under (a).

33. The method of claim 32, wherein said method causes thickening of the epidermis, thereby strengthening the natural protection against the harmful effects of solar radiation or ultraviolet radiation.

34. The method of claim 32, is a method for treating skin or hair pigmentation disorders which is promoting the biosynthesis of melanine.

35. The method of claim 32, wherein said method comprises applying a plant extract containing said xanthine component where in the plant extract is selected from the group consisting of cacao beans, tea leaves, Ilex paraguariensis, cola nitida and cola verticillata.

36. The method of claim 32, wherein the total concentration of the xanthine component ranges between 0.001% and 10% by weight, relative to the total weight of the composition.

37. The method of claim 32, wherein the total concentration of the xanthine component ranges between 0.01 and 1% by weight, relative to the total weight of the composition.

38. The method of claim 32, wherein the xanthine component is incorporated in hydrated lipidic lamellar phases or in liposomes.

39. The method of claim 11, wherein $R_1$ is selected from the group consisting of a methyl, ethyl, propyl and butyl radical.

40. The method of claim 14, wherein said alkali metal salt is selected from the group consisting of sodium, potassium and ammonium; said organic base salt is selected from the group consisting of ethanolamine, diethanolamine, ethylenediamine, isopropylamine, triethanol-amine and octadecylamine.

41. A method of treating the skin or hair for promoting pigmentation, said method comprising applying to said skin or hair to be pigmented, in an amount effective for producing pigmentation, at least one xanthine component wherein:

(a) the xanthine has the formula (I) below:

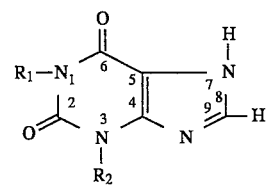

in which:

$R_1$ and R2 are different and are each a hydrogen atom, a linear or branched alkyl radical having from 1 to 8 carbon atoms or a cyclo-alkyl radical having 3 to 8 carbon atoms, one of $R_1$ and $R_2$ being a hydrogen atom, or (b) a pharmaceutically or cosmetically acceptable salt of xanthine of formula (I).

42. The method of claim 41, wherein xanthine is selected from the group consisting of 1-methylxanthine, 1-ethylxanthine, 1-propylxanthine, 1-butylxanthine, 3-methylxanthine, 3-propylxanthine, 3-butylxanthine and 3-isobutylxanthine.

43. The method of claim 41, wherein xanthine is present in a composition in a total concentration ranging between 0.001% and 10% by weight, relatively to the total weight of the composition.

* * * * *